US00PP08084P

United States Patent [19]

Taylor

[11] Patent Number: Plant 8,084

[45] Date of Patent: Jan. 5, 1993

[54] NECTARINE TREE NAMED MAY JIM

[75] Inventor: James W. Taylor, Dinuba, Calif.

[73] Assignee: Ito Packing Company, Reedley, Calif.

[21] Appl. No.: 588,105

[22] Filed: Sep. 25, 1990

[51] Int. Cl.[5] ..... A01H 5/00

[52] U.S. Cl. ..... Plt./41.1

[58] Field of Search ..... Plt./41

*Primary Examiner*—James R. Feyrer

*Attorney, Agent, or Firm*—Dennis B. Haase

[57] ABSTRACT

A new and novel F2 hybrid, large size nectarine tree from "Red Jim"×"May Glow", bearing fruit having yellow, lightly red flecked, very firm meaty flesh which does not cling strongly to very small stones at ripening about the last week in May to the first week in June, with a bright, nearly total red skin color.

1 Drawing Sheet

BACKGROUND OF THE VARIETY

The present invention relates to a new and distinct variety of nectarine tree, which I refer to as May Jim, of a yellow fleshed, cling stone fruit, attractive in appearance, maturing in the early season period, which was developed from a continued fruit breeding program.

ORIGIN AND ASEXUAL REPRODUCTION OF THE NEW VARIETY

This novel nectarine was derived from an ongoing fruit breeding program for the improvement of peaches and nectarines to enhance quality and market acceptability. The flowers of the Red Jim Variety (U.S. Plant Pat. No. 4,518) were emasculated and pollenated wtih pollen from the May Glow nectarine (U.S. Plant Pat. No. 5,245). Seeds produced from this method were stratified and grown to a height of 18 inches. These seedlings were bud grafted into dehorned orchard trees in the experimental orchard of Ito Packing Co., Inc., Reedley, Calif. An F2 generation was then grown from which this selection was propagated into a mature dehorned tree.

As the hybrid clones matured, selections were made and retained. Flowers of such clones were open pollinated and allowed to bear fruit. Stones selected from certain of the selected clones were then planted and seedlings attained were then grafted onto dehorned trees, allowed to produce fruit, and served as an F2 generation for further selection. The tree of this application was selected from the F2 generation as an outstanding variety, and was further grafted on to several dehorned trees. Such testing has shown the clones to be identical to the outstanding selection in every distinguishing respect.

SUMMARY OF THE VARIETY

The instant variety developed through the above methods was selected because of its excellent eating quality, its bright red color, very firm flesh when mature and very early season of maturity.

BRIEF DESCRIPTION OF THE DRAWINGS

The accompanying drawing illustrates typical specimens of the fruit and foliage of my new variety as grown in the San Joaquin Valley of California. Four specimens are shown, one of which is in the side elevation, one showing the apex view, another from the apex view with the apex portion of the fruit cut away to show the explosed flesh, and another with the stem cavity exposed. The pit is illustrated separately.

DETAILED DESCRIPTION

The following is a detailed description of my new variety with color reference being to the Maerz and Paul Distionary of Colors, except in instances where terminology having generally accepted meaning is employed.

Parentage: Red Jim×May Glow F2.

Propagation: Maintains its distinguishing characteristics through several bud grafts.

Locality where grown and observed: Near Reedley, County of Fresno, Calif.

TREE

Size: Large, vigorous, upright, open, vase form; productive, regular bearer.

Trunk: Medium size; medium texture.

Branches: Spreading.

Vigor: Vigorous, productive.

Regularity of bearing: Regular bearer.

Leaves:

*Color.*—Top side — 32B10; underside 3118.

*Size.*—Average length — 15.2 cm; average widty 4.7 cm; medium thickness.

*Margin.*—Glandular; crenate.

*Petiole.*—Medium length; medium thickness.

*Glands.*—Reinform; very small; average number — two; usually two near the base of the leaf on the petiole, one being slightly lower than the other. There may be another on the leaf blade near the base. On occasional leaves, the glands may be wanting or only on the leaf blade.

*Stipules.*—Small; dehisce when leaves are very young.

Flower bud: Medium size.

Flowers: Large; showy; average width 4.8 cm.

Petals: Average width 14 mm; average length 21 mm.

Color: Light pink.

Date of full bloom: About 3 days ahead of May Glow.

Anthers: Light red.

FRUIT

Maturity:

*When described.*—firm ripe, May 20, 1989 on girdled tree; May 27 on nongirdled tree.

Date of first picking: May 20, 1990.
Date of last picking: Jun. 5, 1990.
Size:
*Average axial length.*—6.3 cm; average transverse width in suture plane — 6.1 cm.
*Axial diameter.*—6.15 cm.
Form: Essentially round but compressed at the base.
Suture: In general the ventral suture is shallow from the base to the apex, but may be deeper in occasional fruits. The ventral suture extends to slightly beyond the apex with the apex sunken below the contour of the fruit.
Ventral surface:
*Cavity.*—Round, shallow.
*Base.*—Flat.
*Apex.*—Smooth, recessed in the suture.
*Skin.*—Medium thick; medium texture.
*Tendency to crack.*—None observed.
*Bloom.*—Wanting.
*Color.*—Base color yellow (10J5) but only around the base of the fruit where it is pressed against the limb. As the fruit matures from a basic green yellow color, it becomes very closely speckled with red dots (5J11) which coalesce to solid light red (5J9).
Flesh:
*Texture.*—Very firm, meaty.
*Color.*—Yellow (9J2) with very little red (5E6) around the stone and flecked through the flesh. The red flecks throughout the flesh are very slight and not pronounced around the stone.
*Flavor.*—Good balance of acid and sugar. Soluble solids of 17% (refractometer).
*Juice.*—Abundant.
*Aroma.*—Not very pronounced.
*Fibres.*—Fibres weakly attached around the pit. Short.
*Ripening.*—Even, remains firm on the tree for a long period so that it can be harvested and packed after making its final swell.
*Eating quality.*—Excellent.
Stone:
*Adherence to the flesh.*—Cling stone, but with fibres not attached strongly to the stone when mature.
*Size.*—Small, average thickness 21 mm; average width 26 mm; average length 32 mm.
*Form.*—Oval.
*Hilum.*—Very small.
*Dorsal edge.*—Narrow with rather deep groove adjacent, although all grooves may be shallow in some stones.
*Ventral edge.*—Shallow grooves with slight wing protrusion toward apex.
*Surface.*—Irregular, small grooves and pits.
*Color.*—Brown (7E12).
*Tendency to split.*—Very little for an early season variety.
Use: Fresh market.
Keeping quality: Excellent.
Shipping quality: Excellent.
Resistance to disease: Similar to other glanded varieties of nectarines.

Although this novel variety of nectarine tree possesses the described characteristics as a result of the growing conditions in the Reedley area of Fresno County, Calif., in the central portion of the San Joaquin Valley, it is to be understood that variations of the usual magnitude in characteristics incident to growing conditions, fertilization, pruning and pest control are to be excepted.

Having thus described and illustrated my new nectarine tree, what is new and desired to be secured by Letters Patent is:

1. A new and distinct variety of nectarine tree with fruit of yellow fleshed cling stone type, with slight red flecks throughout the flesh and not pronounced at the stone, substantially as herein shown and described, having a maturity period in the early season, the fruit being essentially round with a compressed base, having bright red skin color and being very firm, and which handles well during packing operations.

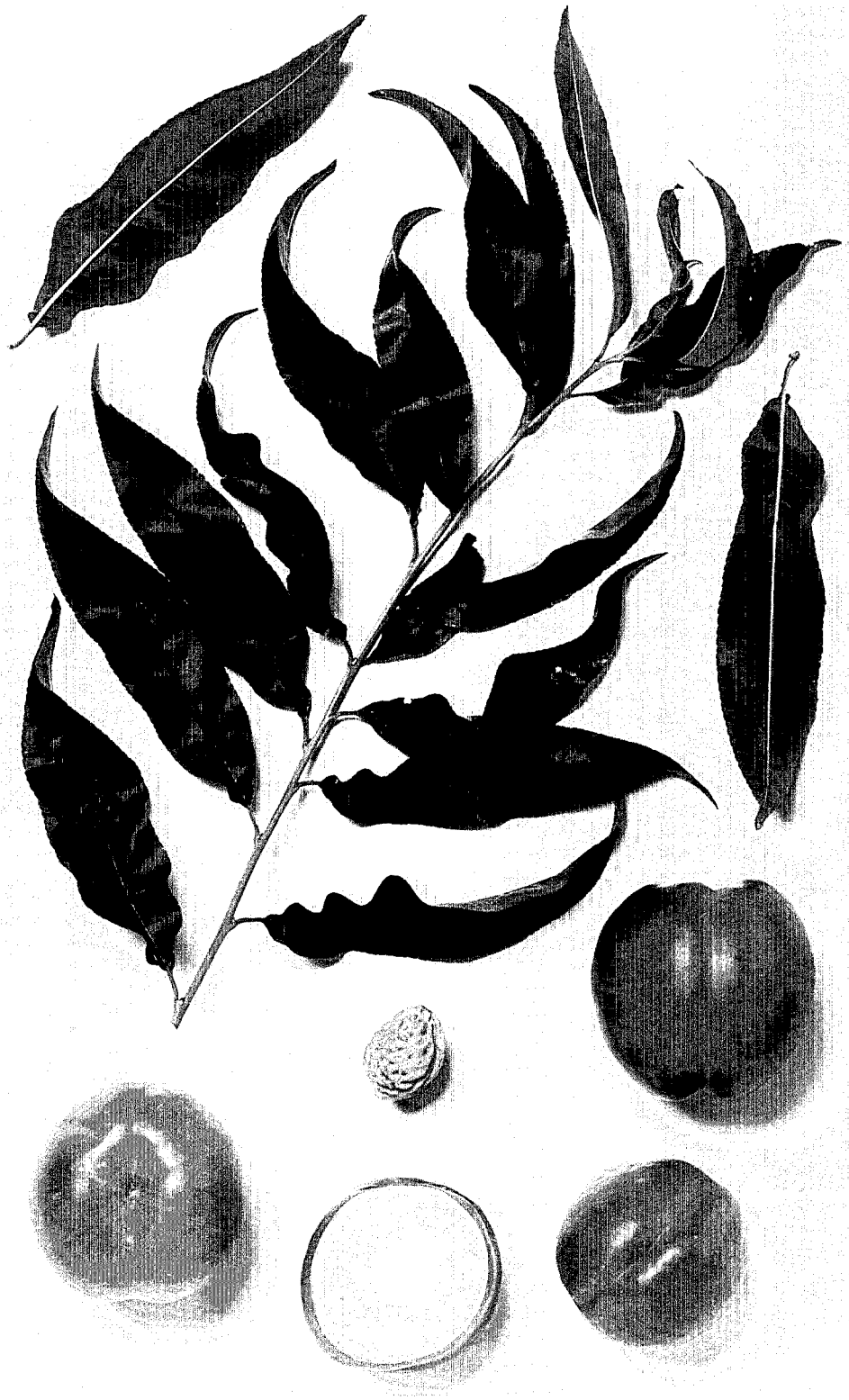

* * * * *